US00PP36426P2

(12) United States Plant Patent
von Tubeuf

(10) Patent No.: US PP36,426 P2
(45) Date of Patent: Feb. 4, 2025

(54) POINSETTIA PLANT NAMED 'NPCW23396'

(50) Latin Name: *Euphorbia pulcherrima*
Varietal Denomination: NPCW23396

(71) Applicant: KLEMM + SOHN GMBH & CO. KG, Stuttgart (DE)

(72) Inventor: Guido von Tubeuf, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/583,843

(22) Filed: Feb. 21, 2024

(51) Int. Cl.
*A01H 5/12* (2018.01)
*A01H 6/38* (2018.01)

(52) U.S. Cl.
USPC ..... Plt./305

(58) Field of Classification Search
USPC ..... Plt./305
See application file for complete search history.

(56) References Cited

PUBLICATIONS

'Lemon xmas' public disclosure 2023 (https://selecta-one.com/katalog/catalogs/04_ONEmagazin_EN/pdf/complete.pdf) retrieved online Jul. 18, 2024 (Year: 2023).*
Nexus of 'NPCW23396' and 'Lemon xmas' (selecta-one.com/Katalog/catalogs/Home_SE-FR_2024/pdf/complete.pdf) retrieved online Jul. 18, 2024 (Year: 2024).*
Nexus of 'NPCW23396' and 'Lemon Glow' (selectanorthamerica.com/Poi nsettias/SeriesInfo/?phid = 050000001014038) Retrieved online Jul. 18, 2024 (Year: 2024).*

* cited by examiner

*Primary Examiner* — Karen M Redden
*Assistant Examiner* — Zachariah Allan Kay
(74) *Attorney, Agent, or Firm* — Weatherly IP Solutions, LLC; James M. Weatherly

(57) ABSTRACT

A new poinsettia plant particularly distinguished by having lime to yellowish bracts with a low vigor, is disclosed.

1 Drawing Sheet

Genus and species: *Euphorbia pulcherrima.*
Variety denomination: 'NPCW23396'.

BACKGROUND OF THE NEW PLANT

The present invention comprises a new and distinct variety of poinsettia, botanically known as *Euphorbia pulcherrima* and hereinafter referred to by the variety name 'NPCW23396'. 'NPCW23396' is a selection from a controlled cross conducted in December 2017 in Nairobi, Kenya of the proprietary female *Euphorbia* line 'NPCW14225' (unpatented) and the commercial male *Euphorbia* line 'Autumn Leaves' (patent status unknown).

Seeds from the cross were selected and plants were grown for evaluation. A plant line was selected in October 2018 in Nairobi, Kenya and named 'NPCW23396'. In May 2016, 'NPCW23396' was first vegetatively propagated by apical cuttings. 'NPCW23396' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Lime to yellowish colour; and
2. Low vigor.

DESCRIPTION OF THE PHOTOGRAPH

This new poinsettia plant is illustrated by the accompanying photograph which shows an overall view of the plant.

The photograph is of a plant approximately twelve-weeks-old, grown indoors in Stuttgart, Germany in December 2023. The colors shown are as true as can be reasonably obtained by conventional photographic procedures.

DESCRIPTION OF THE NEW VARIETY

The following detailed descriptions set forth the distinctive characteristics of 'NPCW23396'. The data which define these characteristics were collected from asexual reproductions carried out in Stuttgart, Germany. Data was collected on eighteen-week-old plants grown indoors in Stuttgart, Germany under greenhouse conditions in January 2024. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW23396'.

Parentage:
- *Female.*—Proprietary female *Euphorbia* line 'NPCW14225' (unpatented).
- *Male.*—Commercial male *Euphorbia* line 'Autumn Leaves' (patent status unknown).

Plant:
- *Form.*—Triangular.
- *Growth habit.*—Upright.
- *Height.*—26 to 28 cm.
- *Width.*—26 to 30 cm.
- *Average number of inflorescences per plant.*—6.

*Keeping quality*.—Very good.
*Time to produce a cutting*.—5 to 6 weeks.
*Flowering response time*.—Approximately 55 days.
*Propagation type*.—Apical cuttings.
*Rooting habit and root color*.—Freely branching and white (NN155C).

Lateral branches:
*Color*.—RHS 139B.
*Length*.—22 to 24 cm.
*Internode length*.—0.5 to 2.0 cm.
*Diameter*.—0.5 to 0.7 cm.
*Branching habit*.—Freely branching.
*Number of lateral branches per plant*.—6 to 7.
*Texture*.—Smooth.
*Strength*.—Sturdy.

Leaves:
*Quantity*.—8 to 9 per lateral branch.
*Arrangement*.—Alternate.
*Number of lobes on the leaf blade*.—1-2.
*Lobation depth*.—Shallow.
*Depth of the deepest sinus of the leaf blade*.—0.5 cm.
*Shape*.—Ovate.
*Apex*.—Acute.
*Base*.—Rounded.
*Margin*.—Almost entire.
*Length*.—6 to 10 cm.
*Width*.—4 to 7 cm.
*Texture*.—Upper: Smooth. Lower: Slightly pubescent.
*Vein color*.—Upper surface: Transparent (veins do not have color and the color of the backside of the leaves are visible). Lower surface: RHS 144D.
*Variegation*.—Absent.
*Venation pattern*.—Reticulate.
*Color*.—Mature foliage: Upper surface: Closest to RHS 139A. Lower surface: Closest to RHS 137A. Immature foliage: Upper surface: RHS 139A to 141B. Lower surface: Closest to RHS 137B.
*Leaf petiole*.—Length: 2 to 4 cm. Diameter: 0.2 to 0.3 cm. Color: Upper (part) surface: RHS 144D. Lower (part) surface: RHS 144D. Texture: Smooth. Strength: Sturdy.
*Transitional leaves*.—Sparse.

Inflorescence:
*Type and habit*.—Cluster of cyathia.
*Quantity per lateral branch*.—1.
*Position relative to foliar plane*.—Below.
*Lastingness of inflorescence on the plant*.—2 months.
*Natural flowering season*.—November/December.
*Diameter*.—18 to 23 cm.
*Height*.—3 to 4 cm.
*Fragrance*.—Absent.

Bracts:
*Number of bracts per inflorescence*.—7-8.
*Shape*.—Ovate.
*Apex*.—Acute.
*Base*.—Rounded.
*Margin*.—Mostly entire.
*Size*.—Length: 6 to 9 cm. Width: 4 to 6 cm.
*Texture (both upper and lower surfaces)*.—Smooth.
*Folding along the main vein*.—Absent.
*Twisting*.—Absent.
*Rugosity between the veins*.—Weak to medium.
*Venation pattern*.—Reticulate.
*Vein color*.—Upper surface: RHS 142B. Lower surface: RHS 142B.
*Bract color*.—Upper surface: RHS 1C to 1D. Lower surface: RHS 1C to 1D.
*Bract petiole*.—Length: 0.5 to 2.0 cm. Diameter: 0.2 to 0.3 cm. Color: Upper (part) surface: RHS 142B. Lower (part) surface: RHS 142B. Texture: Smooth. Strength: Sturdy.

Cyme:
*Diameter*.—1.0 to 1.5 cm.
*Cyathia number*.—4 to 7 per inflorescence.
*Deformation of glands of the cyathium*.—Absent.
*Timing of opening of cyathia*.—First pollen appears in parallel to opening of the nectar cups. Stigmas appear 2 weeks later.
*Cyathium*.—Shape: Ovate. Texture (inner and outer surfaces): Smooth. Diameter: 0.2-0.4 cm. Length: 0.2-0.25 cm. Color: RHS 143B.
*Peduncle*.—Color: RHS 143B. Length: 0.2 cm. Diameter: 0.1 cm. Texture: Smooth. Strength: Sturdy.

Fruit and seed set: None observed.

Disease and insect resistance: No particular disease or insect resistance observed.

COMPARISON WITH PARENTAL LINES AND KNOWN VARIETY

'NPCW23396' is distinguished from its parents as described in Tables 1:

TABLE 1

| Comparison with Parental Lines | | | |
|---|---|---|---|
| Trait or characteristic | Instant variety 'NPCW23396' | Female parent 'NPCW14225' | Male parent 'Autumn Leaves' |
| Bract colour | Lime to yellowish colour | Lime colour | Apricot to orange colour |

COMPARISON WITH SIMILAR VARIETY

'NPCW23396' is most similar to the commercial poinsettia plant named Golden Glo, 'PER1549' (U.S. Plant Pat. No. 31,921). Differences between the two varieties are described in Table 2:

TABLE 2

| Trait | Variety 'NPCW23396' | Commercial line 'Golden Glo' |
|---|---|---|
| Bract colour | Lime to yellowish colour | Yellow colour |
| Vigour | Low | Very low |

I claim:

1. A new and distinct cultivar of Poinsettia Plant Named 'NPCW23396' as described and illustrated herein.

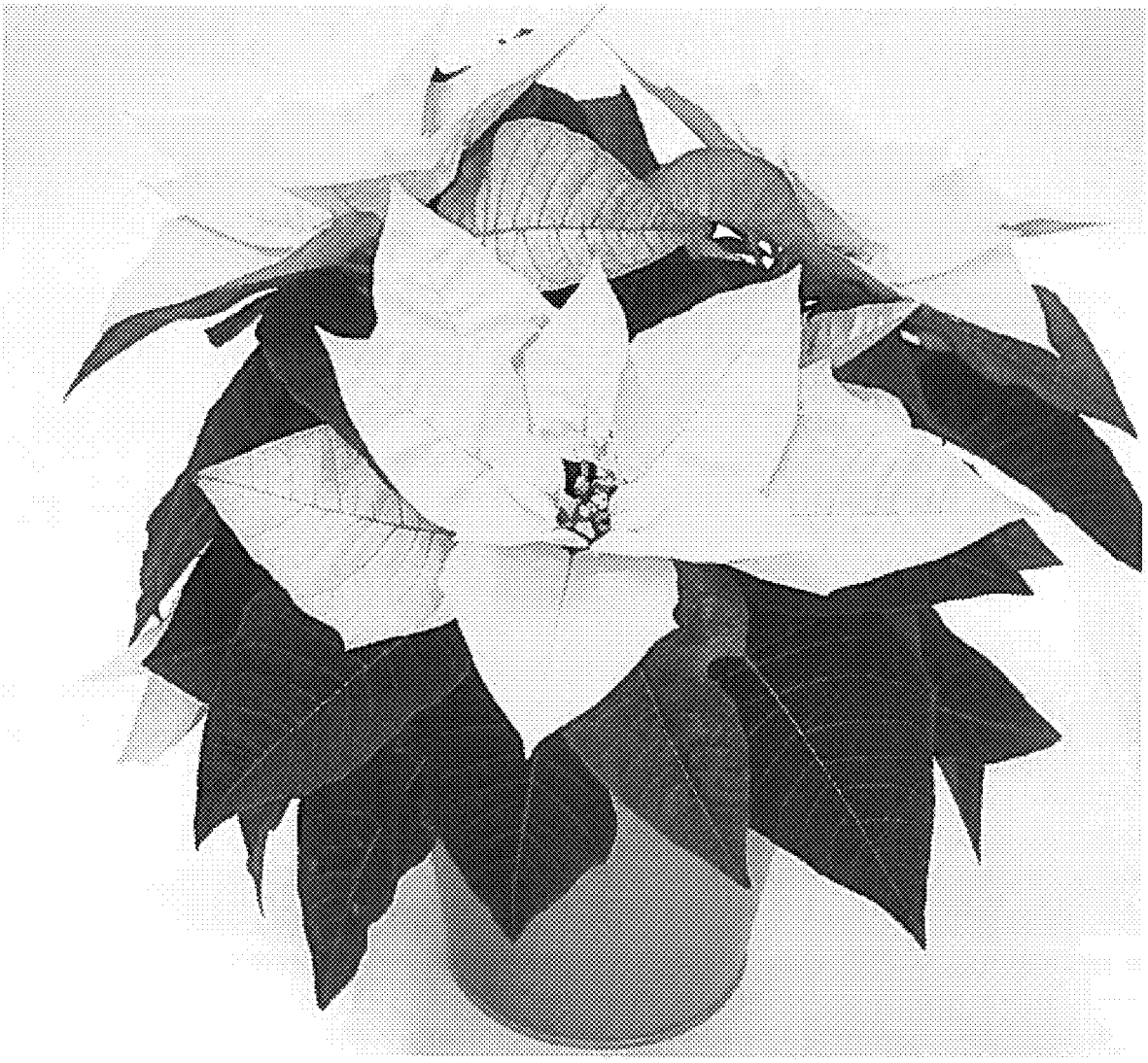

* * * * *